United States Patent [19]

Kojima et al.

[11] 4,347,184

[45] Aug. 31, 1982

[54] PROCESS FOR SEPARATING AND RECOVERING COPROPORPHYRIN AND UROPORPHYRIN FROM A CULTURE BROTH CONTAINING THEM

[75] Inventors: Ichiro Kojima; Kenji Maruhashi, both of Yokohama; Yasuo Fujiwara, Tokyo, all of Japan

[73] Assignee: Nippon Oil Company, Ltd., Tokyo, Japan

[21] Appl. No.: 247,501

[22] Filed: Mar. 25, 1981

[30] Foreign Application Priority Data

Mar. 25, 1980 [JP] Japan .............................. 55-036882

[51] Int. Cl.$^3$ ......................................... C07D 207/00
[52] U.S. Cl. .................................. 260/314; 435/118; 435/119; 435/830
[58] Field of Search ........................................ 260/314

[56] References Cited

PUBLICATIONS

Simirnov Chem. Abst. 17136s vol. 70, 1969.
Joerg Jensen Chem. Abst. 15581g, 1963.

*Primary Examiner*—Jane T. Fan

*Attorney, Agent, or Firm*—Wenderoth, Lind & Ponack

[57] ABSTRACT

A process for separating and recovering coproporphyrin and uroporphyrin from a culture broth containing them, which comprises (1) adjusting the pH of the liquid phase of a cultured broth containing coproporphyrin and uroporphyrin to a range of 2.5 to 4 to form a solid precipitate containing coproporphyrin and uroporphyrin and collecting the precipitate, (2) preparing an aqueous alkaline solution of the solid precipitate obtained in step (1), adjusting the pH of the solution to a range of more than 4 but not over 6, to form a solid precipitate containing coproporphyrin, and collecting the precipitate, and (3) adjusting the pH of the residue left after collection of the precipitate in step (2) to a range of 1 to 4 to form a solid precipitate containing uroporphyrin and collecting the precipitate.

The active porphyrin components thus obtained have physiological activity in regulating various organisms of the body, such as, for example, improving the function of the liver.

1 Claim, No Drawings

PROCESS FOR SEPARATING AND RECOVERING COPROPORPHYRIN AND UROPORPHYRIN FROM A CULTURE BROTH CONTAINING THEM

This invention relates to a process for separating and recovering coproporphyrin and uroporphyrin from a cultured broth containing them industrially advantageously by an easy operation with good efficiency.

More specifically, this invention relates to a process for separating and recovering coproporphyrin and uroporphyrin from a cultured broth containing them, which comprises (1) adjusting the pH of the liquid phase of a cultured broth containing coproporphyrin and uroporphyrin to a range of 2.5 to 4 to form a solid precipitate containing coproporphyrin and uroporphyrin and collecting the precipitate, (2) preparing an aqueous alkaline solution of the solid precipitate obtained in step (1), adjusting the pH of the solution to a range of more than 4 but not over 6, to form a solid precipitate containing coproporphyrin, and collecting the precipitate, and (3) adjusting the pH of the residue left after collection of the precipitate in step (2) to a range of 1 to 4 to form a solid precipitate containing uroporphyrin and collecting the precipitate.

Porphyrins, occuring widely in the tissues of various organisms, are known compounds which are important as constituents of heme protein which has to do with physiological actions such as transport of oxygen within the organisms and catalytic action on oxidation-reduction reactions within the organisms. They are active subtances which in medical applications, show interesting physiological activity in regulating organs, for example in improving function of the liver.

Generally, prophyrins are produced by extraction from hemoglobin in the blood or by cultivation of microorganisms having the ability to produce porphyrins. It is not always easy to isolate the porphyrins with good efficiency from co-existing other components of the tissues. In particular, when they are produced within organisms including microbial cells, both coproporphyrin and uroporphyrin are sometimes produced together. It is desired therefore to develop means capable of separating and recovering them efficiently.

Some methods have been known in the past for separating and recovering coproporphyrin or uroporphyrin from an aqueous system containing either of these, but no method has been known to date for separating and recovering coproporphyrin and uroporphyrin efficiently from a system containing both.

The former include, for example, a method which comprises extracting the aqueous system with a solvent such as acetic acid-ethyl acetate, converting the extracted porphyrin to its methyl ester, and subjecting it to an adsorbent chromatographic procedure using an adsorbent such as alumina [J. Chromatog., 5 (1961) 277-299; Biochem. J., 62 (1966), 78], a method comprising treating the aqueous system with an ion exchange resin [Journal of the Agricultural Chemical Society of Japan, 50 (1976), 41-47], and a method which comprises dissolving the aqueous system in chloroform, filtering the solution, and pouring the filtrate into a large amount of methanol to recrystallize it.

These methods have the disadvantage that the actual operating procedures are complex and the recovery of the porphyrin cannot be performed efficiently. Moreover, these methods cannot be used in separating and recovering both coproporphyrin and uroporphyrin efficiently from a system containing them.

The present inventors knew that *Arthrobacter hyalinus, Arthrobacter pascence,* and their mutants or variants have the ability to produce both coproporphyrin and uroporphyrin, and have made investigations in order to develop a method for separating coproporphyrin and uroporphyrin efficiently by a simple operation from a culture broth obtained by cultivating such coproporphyrin- and uroporphyrin-producing microorganisms. These investigations have led to the discovery that coproporphyrin and uroporphyrin can be separated and recovered singly from such a culture broth containing both of these porphyrins by a simple operation comprising collecting the liquid phase of the culture broth, adjusting its pH to a specified range to form a precipitate containing the two porphyrins, re-dissolving the precipitate under specified pH conditions and adjusting the pH to a specified range to perform re-precipitation.

The investigations of the present inventors have shown that by adjusting the pH of the liquid phase to a range of 4 to 2.5, coproporphyrin and uroporphyrin in the liquid phase can be selectively and easily precipitated; when the resulting solid precipitate containing a mixture of coproporphyrin and uroporphyrin is re-dissolved in the presence of alkali to prepare an aqueous alkaline solution of the solid precipitate and the pH of the solution is adjusted to a range of more than 4 but not over 6, preferably to a range of 4.2 to 6, coproporphyrin can be precipitated selectively with good efficiency; and by adjusting the pH of the residue left after the precipitation of coproporphyrin to a range of 4 to 1, uroporphyrin can be precipitated efficiently.

It is an object of this invention therefore to provide a process for separating and recovering porphyrins industrially advantageously from a system containing both of coproporphyrin and uroporphyrin by an easy operation and with good separating efficiency.

The above and many other objects of this invention will become apparent from the following description.

The culture broth containing coproporphyrin and uroporphyrin to be treated by the process of this invention may be any of culture broths containing these two porphyrins, and no special restriction is imposed on the types of microorganisms to produce porphyrins, the cultivation conditions, etc. For example, it may be a broth containing coproporphyrin and uroporphyrin formed by cocultivation of a coproporphyrin-producing microorganism strain and a uroporphyrin-producing microorganism strain either simultaneously or in an arbitrary sequence. Or it may be a mixture of a culture broth of a coproporphyrin-producing microorganism strain and a culture broth of a uroporphyrin-producing microorganism strain. Preferably, it is a broth formed by cultivating a microorganism strain having the ability to produce both of these porphyrins, particularly a strain having the ability to produce coproporphyrin and uroporphyrin belonging to the genus Arthrobacter.

Such a microorganism capable of producing both coproporphyrin and uroporphyrin is selected from *Arthrobacter hyalinus* (FERM-P No. 3125, ATCC 31263, DSM 867), *Arthrobacter pascens* (ATCC 13346, IFO 12139), and mutants or variants thereof, which are all known. These microorganisms have the ability to produce both coproporphyrin III and uroporphyrin III.

Examples of known microorganisms capable of substantially producing coproporphyrin III alone are *Rho-*

*dopseudomonas spheroides* (ATCC 17023), *Micrococcus lysodeikticus* (IFO 3333, ATCC 4698), *Staphylococcus epidermidis* (IFO 3762; IFO 12993, ATCC 14990), *Saccharomyces cerevisiae* (IFO 0203, ATCC 18824), *Bacillus cereus* (ATCC 14579), *Streptomyces griseus* (ATCC 23345, IFO 3102), *Streptomyces olivaceus* (ATCC 3335), *Mycobacterium smegmatis* (IFO 3082), *Corynebacterium diphtheriae* (ATCC 19409) and *Corynebacterium simplex* (ATCC 6946).

Examples of known microorganisms capable of producing uroporphyrin III alone are *Propionibacterium granulosum* (ATCC 25564) and *Propionibacterium acnes* (ATCC 6919).

In the above exemplification, FERM-P stands for Fermentation Research Institute, Agency of Industrial Science and Technology, Japan; ATCC, for American Type Culture Collection, U.S.A.; IFO, for Institute for Fermentation, Osaka, Japan; and DSM for German Collection of Microorganisms.

The above exemplified porphyrin-producing microorganisms are freely distributable strains deposited in the above depositories under the depository numbers indicated, and those skilled in the art can obtain them easily from these depositories.

The above exemplified microorganisms having the ability to produce both coproporphyrin III and uroporphyrin III are especially preferred for production of the starting broth used in the performance of the process of this invention in that while strains belonging to other genera produce coproporphyrin III in an amount of 10 to 40 mg/liter, and uroporphyrin III in an amount of 4 mg/liter in the culture broth, the above exemplified microorganisms produce coproporphyrin III in an amount of 500 mg/liter (about 10 times) and uroporphyrin III in an amount of 100 mg/liter (25 times).

The liquid phase of the culture broth containing coproporphyrin and uroporphyrin used in the process of this invention can be obtained by removing microbial cells and other solids from a culture broth obtained by using the above-exemplified microorganisms. This can be performed, for example, by centrifugal separation.

Cultivation for the formation of the culture broth can be performed by selecting optimum pH conditions and suitable cultivating conditions near the optimum temperatures which are known for the above-exemplified microorganism strains. For example, in order to obtain a starting culture broth containing coproporphyrin and uroporphyrin which is especially suitable for practising the process of this invention, a strain having the ability to produce coproporphyrin and uroporphyrin belonging to the genus Arthrobacter at a temperature of about 20° C. to about 40° C. at a pH of about 4 to about 9.5. The cultivation period can be suitably selected, and may, for example, be about 2 days to about 30 days.

Examples of suitable nitrogen sources are corn step liquor, yeast extract, meat extract, peptone, amino acids, hydrolyzed proteins, fish meal, ammonium salts, nitric acid salts and urea. They may be used in a combination of two or more. Examples of suitable carbon sources are carbonhydrates, alcohols, hydrocarbons, and bran. They can also be used in a combination of two or more. Examples of mineral sources are phosphoric acid salts, magnesium salts, zinc salts, calcium salts, manganese salts, molybdenum salts and copper salts. They may be used in a combination of two or more.

According to the process of this invention, the pH of the liquid phase of the culture broth containing coproporphyrin and uroporphyrin which can be obtained as above is adjusted to a range of 4 to 2.5, preferably 3.8 to 2.8 to form a solid containing a mixture of coproporphyrin and uroporphyrin. The solid is usually formed as a precipitate, and is collected by any desired solid-liquid separating means such as centrifugal separation, filtration or decantation.

Examples of an acid substance to be used in pH adjustment include inorganic acids such as sulfuric acid, hydrochloric acid, nitric acid and phosphoric acid, and organic acids such as formic acid, acetic acid, oxalic acid and lactic acid.

The solid precipitate can be obtained as a solid composed of coproporphyrin and uroporphyrin which are fairly well selectively separated from carbon sources, nitrogen sources, minerals and other impurities which may be included in the liquid phase of the culture broth.

Then, the solid precipitate is re-dissolved to prepare an aqueous alkaline solution. For this purpose, there can be used any alkaline substance which can dissolve both coproporphyrin and uroporphyrin in concentrations capable of dissolution. Examples of preferred alkalies are sodium hydroxide, potassium hydroxide, sodium carbonate, potassium carbonate and calcium carbonate.

The pH of the aqueous alkaline solution is then adjusted to a range of more than 4 but not over 6, preferably 4.2 to 6, especially preferably 4.4 to 4.8, coproporphyrin in the solution is selectively precipitated, and the precipitated coproporphyrin-containing solid is collected. Thus, a coproporphyrin component of high purity can be separated and recovered. The acid substance utilized for pH adjustment may be the same as those exemplified hereinabove with regard to the formation of a solid precipitate containing both porphyrins. The solid can be collected by filtration, centrifugal separation and other solid-liquid separating means.

The pH of the residue left after separation of the coproporphyrin-containing solid is adjusted to a range of 4 to 1, preferably 3.8 to 1.4, to precipitate a uroporphyrin-containing solid. By collecting the precipitated uroporphyrin-containing solid, a uroporphyrin component having fairly high purity can be separated and recovered. The acidic substance used for pH adjustment may be the same as those exemplified hereinabove. The solid obtained can be collected in the same manner as described above.

According to the process of this invention, coproporphyrin and uroporphyrin can be easily separated (fractionated) in good yields efficiently by an easy operation from the liquid phase of the culture broth containing them as cultivation products. The purifying procedure for these porphyrins can be easily performed. The individual components so recovered can be further purified by conventional means. For example, the purification may be performed by a method which comprises converting each component to its methyl ester with a mixture of methanol and sulfuric acid and chromatographing the methyl ester on a column of alumina, silica gel, etc. and a method which comprises boiling the aforesaid methyl ester in a solvent such as benzene, toluene, pyridine, dichloroethane, and tetrahydrofuran, allowing it to cool to precipitate the purified porphyrin. In performing the process of this invention, the pH adjustment for forming a solid containing coproporphyrin may be carried out after repeating the formation of a solid precipitate containing both coproporphyrin and uroporphyrin and then re-dissolving the solid precipitate a desired number of times.

The following Examples illustrate the process of this invention more specifically.

EXAMPLE 1

*Arthrobacter hyalinus* (FERM P No. 3125) was inoculated in a 500 ml. Erlenmeyer flask containing 200 ml of a sterilized culture medium containing, per liter of deionized water, 10 g of glucose, 1.0 g of yeast extract, 3.0 g of peptone, 3.0 g of ammonium nitrate, 0.4 g of monopotassium phosphate, 1.5 g of disodium phosphate, 5.0 g of magnesium sulfate, 10 mg of manganese sulfate, 10 mg of zinc sulfate, 200 μg of copper sulfate, 10 μg of molybdenum trioxide and 5.0 g of calcium carbonate, and cultivated under shaking at 30° C. for 3 days. Subsequently, a 50% aqueous solution of glucose was added every 2 to 3 days. The concentrations of the products during 17 days' cultivation were 200 mg/liter for coproporphyrin III and 89 mg/liter for uroporphyrin III.

Four liters of the culture broth contained in 20 Erlenmeyer flasks (500 ml) were centrifugally separated at 10,000 G for 10 minutes. The resulting supernatant liquid was adjusted to pH 3.0 with 2 N HCl, and then centrifuged at 1,000 G for 10 minutes to form a precipitate. The precipitate was then dissolved in 1 liter of 1 N aqueous sodium hydroxide, and the pH of the solution was adjusted to 4.7 with 3 N HCl to form a precipitate. By centrifugal separation at 1,000 G for 10 minutes, 790 mg (recovery ratio 99%) of the precipitate was recovered. Thin-layer chromatography of the precipitate led to the determination that there was only one spot. From the visible region absorption spectrum, IR, NMR, melting point, etc. of the methyl ester of the precipitate the product was determined to be coproporphyrin III.

Then, 3 N HCl was added to the supernatant liquid left after the removal of coproporphyrin III to adjust its pH to 2.6 to form a precipitate. By centrifugation at 1,000 G for 10 minutes, 350 mg (recovery ratio 98%) of the precipitate was recovered. Thin-layer chromatography of the precipitate led to the determination that there was only one spot. From the visible region absorption spectrum, IR, NMR, melting point, etc. of the methyl ester of the precipitate, the product was determined to be uroporphyrin III.

EXAMPLE 2

*Arthrobacter pascens* (IFO 12139) was cultivated for 17 days in the same way as in Example 1. The concentration of coproporphyrin III in the culture broth obtained was 80 mg/liter, and the concentration of uroporphyrin therein was 38 mg/liter.

The pH of 4 liters of the culture broth was adjusted to 3.2 with 3 N HCl, followed by centrifugation at 1,000 G for 10 minutes to form a precipitate. The precipitate was dissolved in 1 liter of 1 N aqueous sodium hydroxide. The pH of the solution was adjusted to 4.4 with 3 N HCl to form a precipitate. By centrifugation at 1,000 G for 10 minutes, 320 mg (recovery ratio 100%) of coproporphyrin III was recovered. To the supernatant liquid was added 3 N HCl to adjust the pH to 2.0 to form a precipitate. By centrifugation at 1,000 G for 10 minutes, 151 mg (recovery ratio 99%) of uroporphyrin III was recovered.

What we claim is:

1. A process for separating and recovering coproporphyrin III and uroporphyrin III from a cultured broth containing them, which comprises
   (1) adjusting the pH of the liquid phase of a cultured broth containing coproporphyrin III and uroporphyrin III to a range of 2.5 to 4 to form a solid precipitate containing coproporphyrin III and uroporphyrin III and collecting the precipitate,
   (2) preparing an aqueous alkaline solution of the solid precipitate obtained in step (1), adjusting the pH of the solution to a range of more than 4 but not over 6, to form a solid precipitate containing coproporphyrin III, and collecting the precipitate, and
   (3) adjusting the pH of the residue left after collection of the precipitate in step (2) to a range of 1 to 4 to form a solid precipitate containing uroporphyrin III and collecting the precipitate.

* * * * *